US00PP15649P2

(12) United States Plant Patent
Osiecki

(10) Patent No.: US PP15,649 P2
(45) Date of Patent: Mar. 15, 2005

(54) ***SPATHIPHYLLUM* PLANT NAMED 'POWER PETITE'**

(50) Latin Name: *Spathiphyllum hybrida*
Varietal Denomination: Power Petite

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 404 days.

(21) Appl. No.: 10/287,081

(22) Filed: Nov. 4, 2002

(51) Int. Cl.[7] ..... A01H 5/00
(52) U.S. Cl. ..... Plt./364
(58) Field of Search ..... Plt./364

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of *Spathiphyllum* plant named 'Power Petite', characterized by its compact, symmetrical, bushy, upright and outwardly arching plant habit; relatively small stature, suitable for 10 to 15-cm containers; vigorous and freely clumping growth habit; glossy dark green leaves; early and freely flowering habit; white-colored spathes that are positioned above the foliage on strong and erect peduncles; and good postproduction longevity.

1 Drawing Sheet

Botanical classification/cultivar designation: *Spathiphyllum hybrida* cultivar Power Petite.

BACKGROUND OF THE INVENTION

The present Invention relates to a new and distinct cultivar of *Spathiphyllum* plant, botanically known as *Spathiphyllum hybrida*, and hereinafter referred to by the cultivar name Power Petite.

The new cultivar is a product of a planned and controlled breeding program conducted by the Inventor in Altha, Fla. The objective of the breeding program is to create new compact and vigorous *Spathiphyllum* cultivars.

The new cultivar originated from a cross-pollination made by the Inventor in July, 1994 of a proprietary *Spathiphyllum hybrida* seedling selection identified as code number 91-FF-1, not patented, as the female or seed parent and the *Spathiphyllum hybrida* cultivar S9, disclosed in U.S. Plant Pat. No. 9,901, as the male or pollen parent. The cultivar Power Petite was discovered and selected by the Inventor as a single plant within the progeny of the stated cross-pollination in a controlled environment in Altha, Fla., in July, 1995.

Asexual propagation of the new cultivar by tissue culture since November, 1998, in a laboratory in Altha, Fla., has shown that the unique features of this new *Spathiphyllum* plant are stable and reproduced true to type in successive generations of asexual propagation.

SUMMARY OF THE INVENTION

The new *Spathiphyllum* has not been observed under all possible environmental conditions. The phenotype may vary somewhat with variations in environment such as temperature and light intensity without, however, any variance in genotype.

The following traits have been repeatedly observed and are determined to be the unique characteristics of 'Power Petite'. These characteristics in combination distinguish 'Power Petite' as a new and distinct *Spathiphyllum* cultivar:

1. Compact, symmetrical, bushy, upright and outwardly arching plant habit; relatively small stature, suitable for 10 to 15-cm containers.
2. Vigorous and freely clumping growth habit.
3. Glossy dark green leaves.
4. Early and freely flowering habit.
5. White-colored spathes that are positioned above the foliage on strong and erect peduncles.
6. Good postproduction longevity.

Plants of the new *Spathiphyllum* can be compared to plants of the female parent, the selection 91-FF-1. In side-by-side comparisons conducted in Altha, Fla., plants of the new *Spathiphyllum* differed from plants of the selection 91-FF-1 in the following characteristics:

1. Plants of the new *Spathiphyllum* were smaller and more compact than plants of the selection 91-FF-1.
2. Plants of the new *Spathiphyllum* had a more vigorous and freely clumping growth habit than plants of the selection 91-FF-1.
3. Plants of the new *Spathiphyllum* flowered earlier and were more freely flowering than plants of the selection 91-FF-1.
4. Leaves of plants of the new *Spathiphyllum* were smaller and had shorter petioles than leaves of plants of the selection 91-FF-1.
5. Spathes of plants of the new *Spathiphyllum* were smaller and were positioned closer to the foliage than spathes of plants of the selection 91-FF-1.

Plants of the new *Spathiphyllum* can be compared to plants of the male parent, the cultivar S9. In side-by-side comparisons conducted in Altha, Fla., plants of the new *Spathiphyllum* differed from plants of the cultivar S9 in the following characteristics:

1. Plants of the new *Spathiphyllum* were more compact and more outwardly arching than plants of the cultivar S9.
2. Plants of the new *Spathiphyllum* had a more vigorous and freely clumping growth habit than plants of the cultivar S9.

3. Plants of the new *Spathiphyllum* were more freely flowering than plants of the cultivar S9.
4. Leaves of plants of the new *Spathiphyllum* were larger, darker green and glossier than leaves of plants of the cultivar S9.
5. Spathes of plants of the new *Spathiphyllum* were larger and had thicker peduncles than spathes of plants of the cultivar S9.

Plants of the new *Spathiphyllum* can be compared to plants of the *Spathiphyllum* cultivar Petite, not patented. However, in side-by-side comparisons conducted in Altha, Fla., plants of the new *Spathiphyllum* differed from plants of the cultivar Petite in the following characteristics:

1. Plants of the new *Spathiphyllum* were more compact, more outwardly arching and bushier than plants of the cultivar Petite.
2. Plants of the new *Spathiphyllum* had a more vigorous and freely clumping growth habit than plants of the cultivar Petite.
3. Plants of the new *Spathiphyllum* flowered earlier and were more freely flowering than plants of the cultivar Petite.
4. Leaves of plants of the new *Spathiphyllum* were larger, darker green and glossier than leaves of plants of the cultivar Petite.
5. Spathes of plants of the new *Spathiphyllum* were positioned closer to the foliage on thicker, stronger and shorter peduncles than spathes of plants of the cultivar Petite.

Plants of the new *Spathiphyllum* can also be compared to plants of the *Spathiphyllum* cultivar S4, disclosed in U.S. Plant Pat. No. 10,013. However, in side-by-side comparisons conducted in Altha, Fla., plants of the new *Spathiphyllum* differed from plants of the cultivar S4 in the following characteristics:

1. Plants of the new *Spathiphyllum* were smaller, more compact, more outwardly arching and bushier than plants of the cultivar S4.
2. Plants of the new *Spathiphyllum* had a more vigorous and freely clumping growth habit than plants of the cultivar S4.
3. Leaves of plants of the new *Spathiphyllum* were broader and glossier than leaves of plants of the cultivar S4.
4. Spathes of plants of the new *Spathiphyllum* were positioned closer to the foliage on thicker, stronger and shorter peduncles than spathes of plants of the cultivar S4.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Spathiphyllum.*

The photograph at the top of the first sheet comprises a side perspective view of a typical plant of 'Power Petite' grown in a 15-cm container.

The photograph at the bottom of the sheet comprises a close-up view of typical inflorescences and leaves of 'Power Petite'.

DETAILED BOTANICAL DESCRIPTION

The aforementioned photographs and following observations and measurements describe 47-week old plants (from planting rooted tissue-cultured plantlets) grown in Altha, Fla., in a polycarbonate-covered greenhouse and under commercial production conditions in 15-cm containers with a single plantlet per container. During the production of the plants, day temperatures ranged from 24 to 32° C., night temperatures ranged from 22 to 25° C. and light levels were about 800 to 1,200 foot-candles.

In the following description, color references are made to The Royal Horticultural Society Colour Chart, 1995 Edition, except where general terms of ordinary dictionary significance are used.

Botanical classification: *Spathiphyllum hybrida* cultivar Power Petite.

Parentage:

*Female parent.*—Proprietary *Spathiphyllum hybrida* seedling selection identified as code number 91-FF-1, not patented.

*Male parent.*—*Spathiphyllum hybrida* cultivar S9, disclosed in U.S. Plant Pat. No. 9,901.

Propagation:

*Type.*—By tissue culture.

*Time to initiate roots on a tissue-cultured cutting.*—Summer: About 18 to 21 days at 25 to 30° C. soil temperature. Winter: About 24 to 28 days at 22 to 27° C. soil temperature.

*Time to produce a fully-rooted tissue-cultured plantlet.*—Summer: About 105 days at 25 to 30° C. soil temperature. Winter: About 119 days at 22 to 27° C. soil temperature.

*Root description.*—Primary roots, very thick and fleshy; lateral branch roots, fine; primary and lateral roots white in color and numerous.

Plant description:

*Plant shape.*—Compact, upright, outwardly arching and symmetrical plant habit; relatively small stature, plants of the new *Spathiphyllum* are typically grown in 10 to 15-cm containers.

*Growth habit.*—Erect when young, becoming outwardly arching as leaves develop. Freely clumping and bushy full appearance; about 10 clumps per plant. Vigorous growth habit and rapid growth rate; from tissue-cultured plantlets, about 11 months are required to produce finished flowering plants in 15-cm containers.

*Plant height.*—About 16 cm from soil level to top of leaf plane and about 44 cm from soil level to spathe apices.

*Plant spread.*—About 52 cm.

*Foliage description.*—Length: About 20 cm. Width: About 9.25 cm. Shape: Ovate. Apex: Acuminate, elongated. Base: Obtuse. Margin: Entire; undulate. Aspect: Initially upright, then outwardly arching; leaves curved downward towards the apex. Surface: Midrib and lateral veins sunken on upper surface and prominent on lower surface; upper surface of blade convex between veins, lower surface of blade concave between veins; upper and lower surfaces rugose. Texture, upper and lower surfaces: Leathery, smooth, glabrous, durable and flexible. Luster, upper and lower surfaces: Glossy; young leaves glossier than fully expanded leaves. Venation pattern: Pinnate; about 14 pairs of primary veins per leaf. Color:

Young leaves, upper surface: More green than 147A. Young leaves, lower surface: More green than 147B. Fully expanded leaves, upper surface: Darker than 147A. Fully expanded leaves, lower surface: Darker than 147B. Midvein and lateral veins, upper surface: Darker than 147A. Midvein, lower surface: 144A. Lateral veins, lower surface: Close to 146D. Petiole: Length: About 14.75 cm. Diameter, just below the geniculum: About 3 mm. Petiole sheath, length: About 13 cm. Petiole sheath, width at midpoint, unfurled: About 7 mm. Petiole sheath, apex: Rounded. Geniculum length: About 7 mm. Geniculum diameter: About 5 mm. Geniculum aspect: Straight to curved. Color: Petiole: Close to 147A. Petiole sheath: Close to 147A. Geniculum: Close to 144A.

Inflorescence description:

*Inflorescence arrangement/quantity.*—Concave spathes with spadices held above the foliage on strong and erect peduncles. Freely flowering; typically at least three developing and open spathes per plant at one time; inflorescences arise from the petiole sheath.

*Time to flower.*—Plants start flowering about 29 weeks after planting rooted tissue-cultured plantlets.

*Inflorescence longevity.*—Spathes generally maintain white color for about 4 to 4.5 weeks on the plant becoming eventually entirely green with subsequent development. As cut flowers, spathes maintain good substance for about one to two weeks.

*Fragrance.*—Faintly fragrant, sweet, typical of *Spathiphyllum.*

*Inflorescence buds.*—Length: About 5 cm. Diameter, widest point: About 5 mm. Shape: Columnar. Color: Close to 155A.

*Spathe.*—Length: About 10.5 cm. Width: About 6 cm. Depth: About 1.9 cm. Shape: Ovate. Apex: Acuminate, elongated; slightly twisted. Base: Obtuse. Aspect: Concave. Color: Front and back surfaces: Close to 155D; midrib, 144A to more green than 147A. Front and back surfaces with subsequent development: 144A; midrib, close to 144A to more green than 147A.

*Spadix.*—Length: About 5 cm. Diameter: About 1.4 cm. Color: Close to 158A gradually becoming close to 144A with subsequent development. Quantity of flowers per spadix: About 105. Stamens: Anthers and filaments minute. Pollen: Scarce. Pollen color: Close to 158D, becoming closer to 158A with subsequent development. Pistils: Conical; pistillate flowers extend about 3 mm beyond the staminate flowers; close to 158A in color.

*Peduncle.*—Length: About 29 cm. Diameter, at midpoint: About 3 mm. Aspect: Straight, erect. Color: Close to 146A.

*Fruit/seed.*—Fruit and seed production have not been observed.

Disease/pest resistance: Plants of the new *Spathiphyllum* have not been observed to be resistant to pathogens or pests common to *Spathiphyllum.*

It is claimed:

1. A new and distinct cultivar of *Spathiphyllum* plant named 'Power Petite', as illustrated and described.

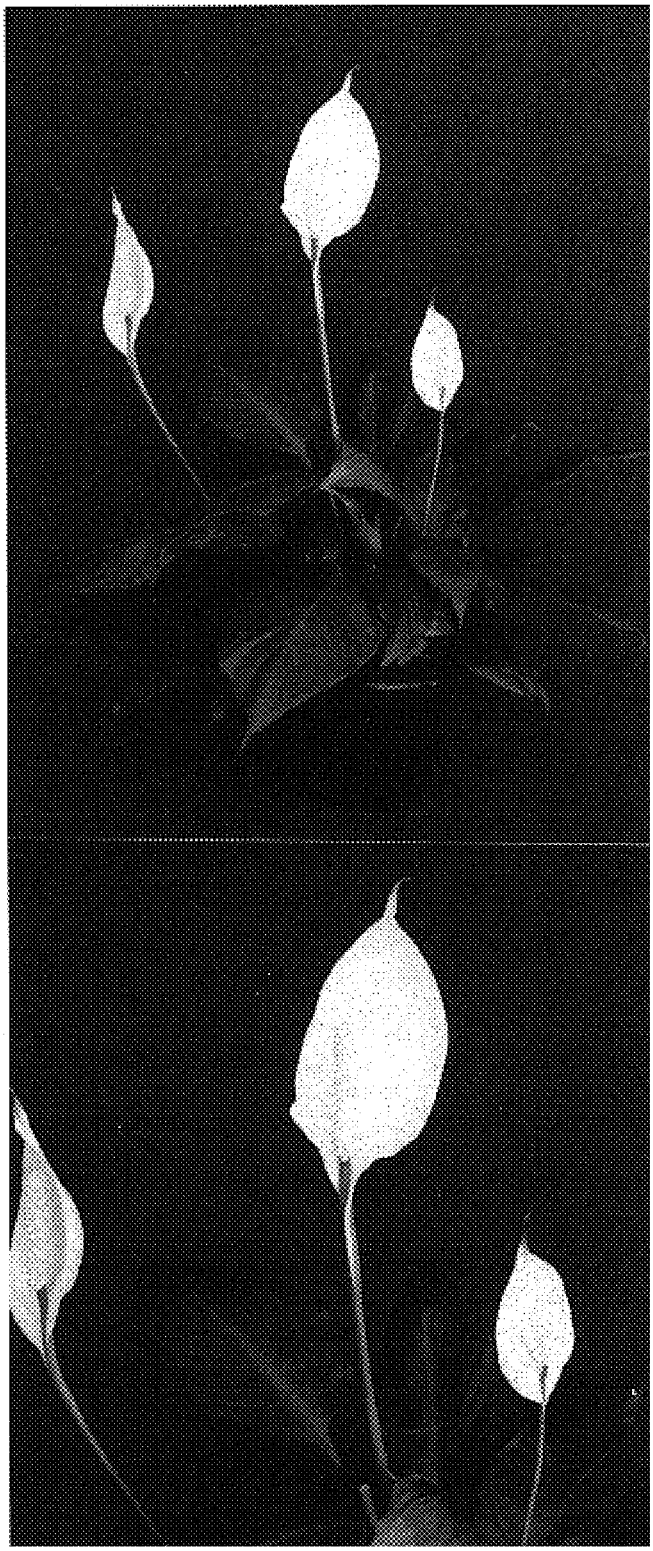

* * * * *